United States Patent
Harman et al.

(10) Patent No.: US 6,477,783 B1
(45) Date of Patent: Nov. 12, 2002

(54) GYRATORY COMPACTOR ANGLE MEASUREMENT DEVICE

(75) Inventors: Thomas Philip Harman, Ellicott City, MD (US); Paul Andrew Fuchs, Jr., Leesburg, VA (US); Thomas Emil Brovold, Edina, MN (US)

(73) Assignee: The United States of America as represented by the Secretary of Transportation, Washington, DC (US)

( * ) Notice: Subject to any disclaimer, the term of this patent is extended or adjusted under 35 U.S.C. 154(b) by 0 days.

(21) Appl. No.: 09/664,707

(22) Filed: Sep. 19, 2000

(51) Int. Cl.[7] .............................. G01B 5/24; G01N 3/08
(52) U.S. Cl. ............................. 33/534; 33/1 N; 33/542; 33/551; 33/555; 73/824; 73/818
(58) Field of Search ........................ 33/1 N, 534, 542, 33/549, 551, 552, 555, 531, 501.02, 501.03; 73/841, 824, 818, 815, 813, 795, 794

(56) References Cited

U.S. PATENT DOCUMENTS

| | | | |
|---|---|---|---|
| 4,087,918 A | * 5/1978 | Schmid et al. | 33/542 |
| 5,456,118 A | * 10/1995 | Hines et al. | 73/818 |
| 5,824,913 A | * 10/1998 | Pyle | 73/818 |

* cited by examiner

*Primary Examiner*—Diego Gutierrez
*Assistant Examiner*—Travis Reis
(74) *Attorney, Agent, or Firm*—Otto M. Wildensteiner

(57) ABSTRACT

An angle measuring device for use in a gyratory compactor. The device is a self-contained unit which is placed in the bottom of the mold and the asphalt or other material being compacted is placed on top of it. Inside the device is a carrier which has two vertically aligned probes which project out from it and touch the walls of the mold. One probe is fixed to the carrier; the other can move independently of the carrier. The difference in extension between the two probes is related to the angle of compaction.

15 Claims, 1 Drawing Sheet

GYRATORY COMPACTOR ANGLE MEASUREMENT DEVICE

STATEMENT OF GOVERNMENT INTEREST

The present invention may be made or used by or on behalf of the Government of the United States without the payment of any royalties thereon or therefor.

BACKGROUND

Gyratory compactors are used to compact asphalt mixture specimens, among other substances. The measured properties of the compacted specimens are used to assess and predict pavement performance. Compaction in a gyratory compactor is achieved by applying a vertical consolidation force while the mold gyrates at a nominally constant angle. This angle is referred to as the angle of gyration. All gyratory compactors have a means for setting the angle of gyration, but it is desirable to have an independent means of verifying the angle since the angle is so critical to the measured properties of the compacted asphalt mixtures. Further, the angle is quite small and a slight variation from the desired angle makes a substantial change in the properties of the compacted asphalt mixture. It is also desirable to be able to measure the angle while the asphalt mixture is being compacted in order to detect any problems with the compactor as soon as they occur.

All compactors use a common mold to contain the asphalt being compacted; ideally, an angle measurement device would fit within this mold, thereby being usable in any compactor.

OBJECTS OF THE PRESENT INVENTION

Accordingly, it is an object of the present invention to provide an angle measuring device for gyratory compactors which can be used with any compactor.

It is a further object of the present invention to provide an angle measuring device for gyratory compactors which provides a very accurate measurement of the angle of compaction.

It is a further object of the present invention to provide an angle measuring device for gyratory compactors which is placed within the mold in which the asphalt is being compacted.

It is a further object of the present invention to provide an angle measuring device for gyratory compactors which is a compact self-contained unit.

SUMMARY

Briefly, the present invention is a self-contained unit which is placed in the bottom or top of the mold along with the asphalt mixture. The unit has two probes, in vertical alignment, which project out from its side and contact the inside of the mold. The probes are on a common carrier that is spring-biased outward in order to cancel out small amounts of off-center alignment of the unit within the mold. One probe is fixed relative to the carrier, the other can move independently of the carrier. The device is placed in the bottom of the mold of a gyratory compactor and the asphalt to be compacted is placed on top of it. As the mold oscillates, the independently-movable probe extends more than and less than the stationary probe; the difference in extensions is related to the angle of the mold and hence the angle of compaction.

DESCRIPTION OF THE PREFERRED EMBODIMENT

Unit 10 of the present invention comprises a housing 12 which is somewhat smaller in diameter than the inside of a standard gyratory compactor mold and about 2.6 inches thick. It is made of steel in order to withstand the heat of the hot asphalt that is placed on top of it and to withstand the pressure of the ram that applies the compaction pressure.

Figure 2:
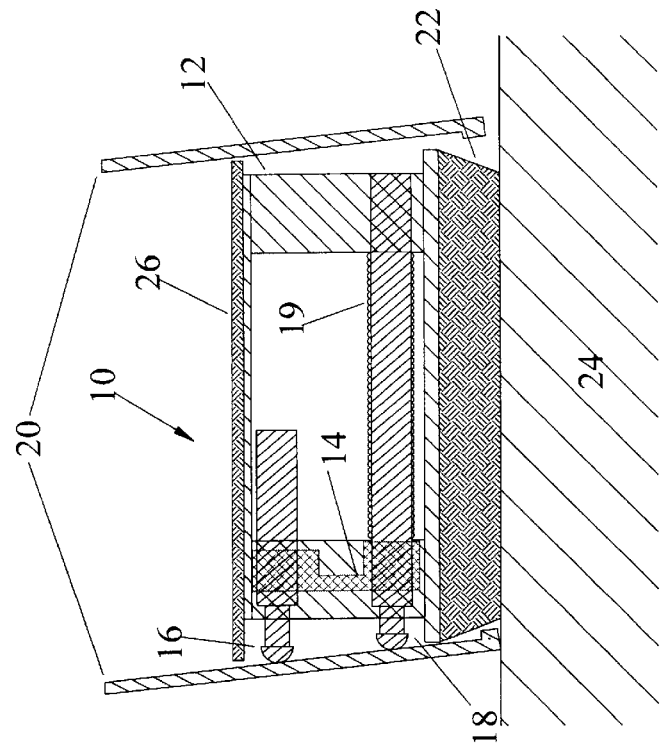
FIG. 2, taken along line A—A in FIG. 1, shows a cross section of the device of the present invention.
Figure 1:
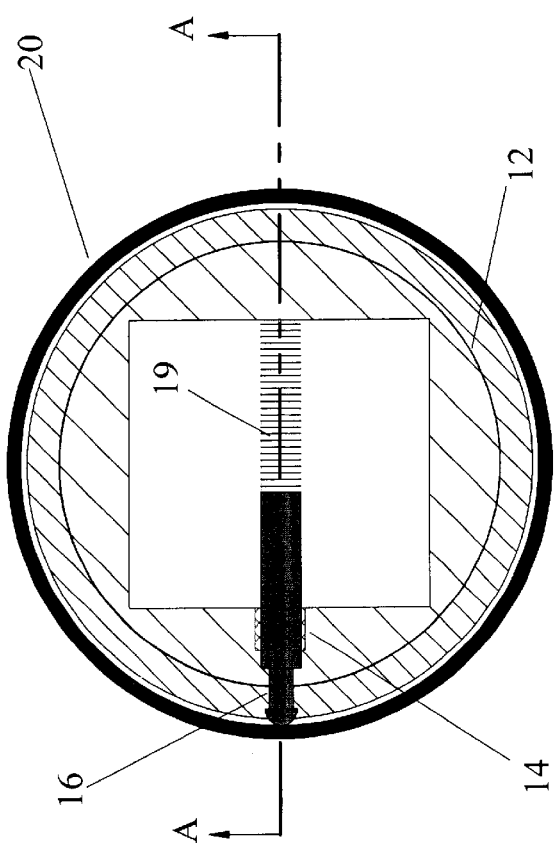
FIG. 1 shows a partial cutaway top view of the device of the present invention placed within the mold in a gyratory compactor.

Inside housing 12 is a carrier 14 which has two probes 16 and 18. Carrier 14 is biased outward by spring 19 in order to keep probes 16 and 18 in contact with the interior wall of mold 20 as mold 20 oscillates. Probe 18 is fixed to carrier 14, which can move relative to housing 12; the force of spring 19 causes the tip of probe 18 to remain in contact with the interior wall of mold 20. Probe 16 is a linear variable differential transformer, or LVDT, which has a tip that is internally spring biased outward and can move independently of probe 18 and carrier 14. Thus when mold 20 is vertical probes 16 and 18 project outward from carrier 14 equal distances; when mold 20 is at an angle as shown in FIG. 2, the tip of LVDT 16 projects outward a greater distance than probe 18, and this difference is a function of the angle of mold 20.

As is well known in the art, base 22 of mold 20 fits loosely within mold 20. As mold 20 is oscillated about its axis, base 22, which rests on horizontal platform 24 in the gyratory compactor, remains horizontal. Probe 18 is kept in contact with the interior wall of mold 20 by spring 19 which forces carrier 14 outward. As mold 20 is oscillated the tip of LVDT 16 moves in and out relative to probe 18, thereby providing a constant, real-time indication of the angle of mold 20 and thereby the angle of compaction.

There is also a top plate 26 which sits on top of unit 10 and both protects it from the asphalt (as well as keeping it from being stuck to the asphalt) and prevents asphalt from being forced between unit 10 and mold 20.

Unit 10 also contains within it a printed circuit board (not shown) which contains the usual power conditioning circuitry, etc. as is well known in the art for this application. The circuit board also contains software that reads the displacement information from LVDT 16, performs an internal calibration, and then stores the information in memory. It interfaces with an external computer (not shown) which downloads the information and converts it to angular data, which can be displayed on a monitor in real time if desired. This allows the user to determine the performance of the gyratory compactor in real time, thereby allowing maximum possible control over the batch mixing process.

LVDT 16 is manufactured and sold by RDP Electrosense, Inc. of Pottstown, PA and is designated as Model D5/100AG. The electronics within the device can be from any manufacturer, as long as they perform the functions described above, as is well known in the art. Likewise, the software in the remote computer can be of any type that provides the capability of saving and loading data sets, instrumentation setup, instrument test and calibration, and data analysis and presentation, all as is well known in the art.

Alternatively, one or both of probes 16 and 18 can be a non-contact probe if such is desired. All that is required is that there be two means for measuring the distance to the inside of the mold from a common reference, and that the two means for measuring the distances be vertically aligned and displaced vertically from each other. If contact probes are used, their tips must have the same radius of curvature in the horizontal plane so that if the probes are not on an exact radius of the mold the distances measured will be consistent.

We claim:

1. In a gyratory compactor having a mold which holds material being compacted at an angle, said mold having an interior wall, a device for measuring the angle of compaction of said material during operation of the compactor comprising self-contained means for placement within said mold underneath the material being compacted, said self-contained means measuring a distance which is related to said angle of compaction and transmitting said distance to recording means outside of said compactor.

2. A gyratory compactor as in claim 1 wherein said device contains two means for contacting the interior wall of said old at two points.

3. A gyratory compactor as in claim 2 wherein said two means for contacting said wall are vertically displaced from each other and are in vertical alignment.

4. A gyratory compactor as in claim 3 wherein said two means for contacting the interior wall of said mold are mounted on a common carrier.

5. A gyratory compactor as in claim 4 wherein one of said means for contacting the interior wall causes said common carrier to move as a unit.

6. A gyratory compactor as in claim 5 wherein the other of said means for contacting the interior wall moves independently of said common carrier.

7. In a gyratory compactor having a mold which holds material being compacted at an angle, a device to be placed underneath the material being compacted for measuring the angle of compaction of said material while said compactor is in operation comprising first means for measuring the displacement of the inside of the mold at a first point, second means for measuring the displacement of the inside of the mold at a second point, and means for transmitting the difference between said displacements to recording means outside of said compactor.

8. A gyratory compactor as in claim 7 wherein said first displacement measuring means and said second displacement measuring means are vertically displaced from each other.

9. A gyratory compactor as in claim 8 wherein said first displacement measuring means and said second displacement measuring means are in vertical alignment.

10. A gyratory compactor as in claim 9 wherein both of said displacement measuring means are on a common carrier.

11. A gyratory compactor as in claim 10 wherein one of said displacement measuring means can move relative to the other.

12. In a gyratory compactor having a mold which holds material being compacted at an angle, said mold having an inside, a method of measuring the angle of compaction of said material while said compactor is in operation which comprises placing underneath the material being compacted a device having the capability of measuring the displacement of the inside of the mold at two points, measuring the displacement of the inside of the mold at a first point, measuring the displacement of the inside of the mold at a second point, and determining the difference between said displacements.

13. The method of claim 12 wherein said first and said second points are in vertical alignment.

14. The method of claim 12 wherein said first and said second points are vertically displaced from each other.

15. The method of claim 14 further comprising transmitting said measurements to recording means outside of said compactor.

* * * * *